(12) United States Patent
Barrow-Williams et al.

(10) Patent No.: US 9,463,282 B2
(45) Date of Patent: Oct. 11, 2016

(54) ARRANGEMENT FOR COUPLING A PLUNGER TO EITHER A SYRINGE OR A STOPPER

(75) Inventors: Timothy Donald Barrow-Williams, Herts (GB); Yannick Hourmand, Haslingfield (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 470 days.

(21) Appl. No.: 13/876,786

(22) PCT Filed: Oct. 6, 2011

(86) PCT No.: PCT/EP2011/067488
§ 371 (c)(1),
(2), (4) Date: Mar. 28, 2013

(87) PCT Pub. No.: WO2012/045827
PCT Pub. Date: Apr. 12, 2012

(65) Prior Publication Data
US 2013/0190694 A1    Jul. 25, 2013

Related U.S. Application Data

(60) Provisional application No. 61/432,261, filed on Jan. 13, 2011.

(30) Foreign Application Priority Data

Oct. 8, 2010   (EP) ..................... 10186978

(51) Int. Cl.
| A61M 5/315 | (2006.01) |
| A61M 5/20  | (2006.01) |
| A61M 5/31  | (2006.01) |
| A61M 5/32  | (2006.01) |

(52) U.S. Cl.
CPC ....... *A61M 5/31513* (2013.01); *A61M 5/2033* (2013.01); *A61M 5/3129* (2013.01); *A61M5/3204* (2013.01); *A61M 5/3232* (2013.01); *A61M 5/31511* (2013.01); *A61M 2005/206* (2013.01); *A61M 2005/2073* (2013.01); *A61M 2005/3107* (2013.01)

(58) Field of Classification Search
CPC .......... A61M 5/3129; A61M 5/3232; A61M 5/31513; A61M 5/31515; A61M 5/31511; A61M 2005/2073; A61M 2005/206
See application file for complete search history.

(56) References Cited

U.S. PATENT DOCUMENTS

2009/0054838 A1*   2/2009   Harrison .................. 604/135
2009/0312705 A1*  12/2009   Grunhut ............. A61M 5/2033
                                                          604/110

(Continued)

FOREIGN PATENT DOCUMENTS

| WO | 2005115511 A1 | 12/2005 |
| WO | 2008113864 A1 | 9/2008  |
| WO | 2009081103 A1 | 7/2009  |

*Primary Examiner* — Theodore Stigell
*Assistant Examiner* — Amber Stiles
(74) *Attorney, Agent, or Firm* — Fish & Richardson P.C.

(57) ABSTRACT

An arrangement for coupling a plunger to either a syringe or a stopper arranged in the syringe. The arrangement includes a syringe holder which is slidably arranged in a housing. The syringe holder is provided with at least one resilient syringe holder arm arranged distally, the syringe holder arm having an inclined surface for bearing against a shoulder, which is arranged at the plunger. The syringe holder arm is supportable by an inner surface of the housing in order to prevent it from being flexed outward in a first position. A widened portion is provided in the housing for allowing the syringe holder arm to flex outwards and disconnect from the plunger when in a more proximal position so as to switch load of the plunger from the syringe to the stopper.

20 Claims, 4 Drawing Sheets

(56) References Cited

U.S. PATENT DOCUMENTS

| | | | |
|---|---|---|---|
| 2013/0096512 A1* | 4/2013 | Ekman et al. | 604/197 |
| 2013/0150801 A1* | 6/2013 | Ekman et al. | 604/198 |
| 2013/0310759 A1* | 11/2013 | Hourmand et al. | 604/198 |
| 2013/0317446 A1* | 11/2013 | Hourmand et al. | 604/196 |
| 2013/0317448 A1* | 11/2013 | Hourmand et al. | 604/197 |
| 2013/0345643 A1* | 12/2013 | Hourmand et al. | 604/198 |
| 2014/0135705 A1* | 5/2014 | Hourmand et al. | 604/196 |

* cited by examiner

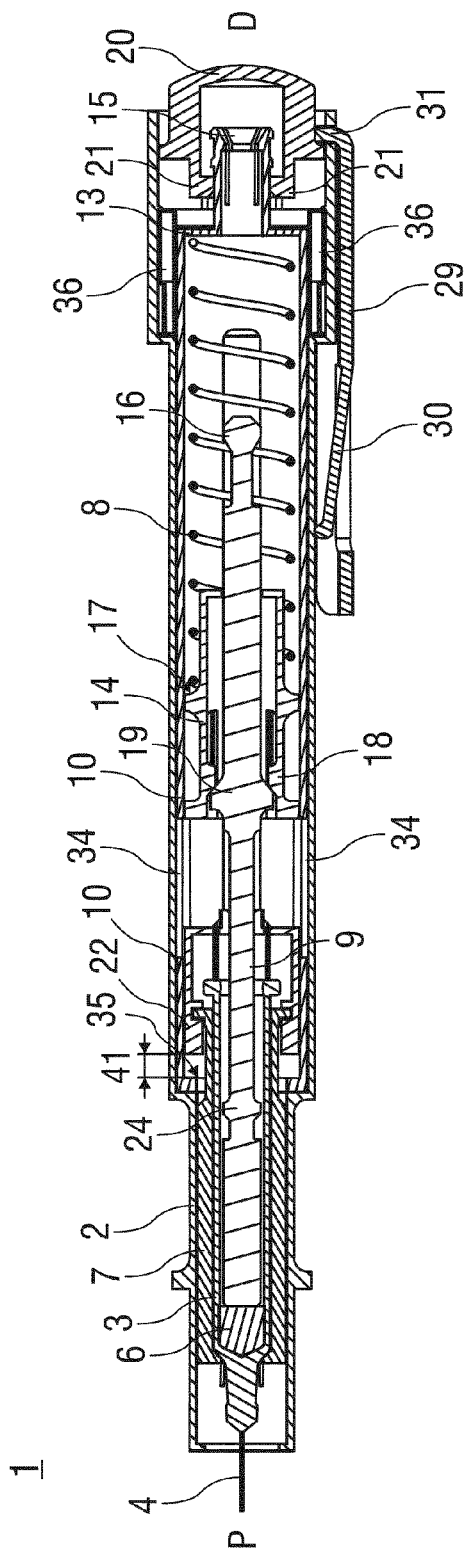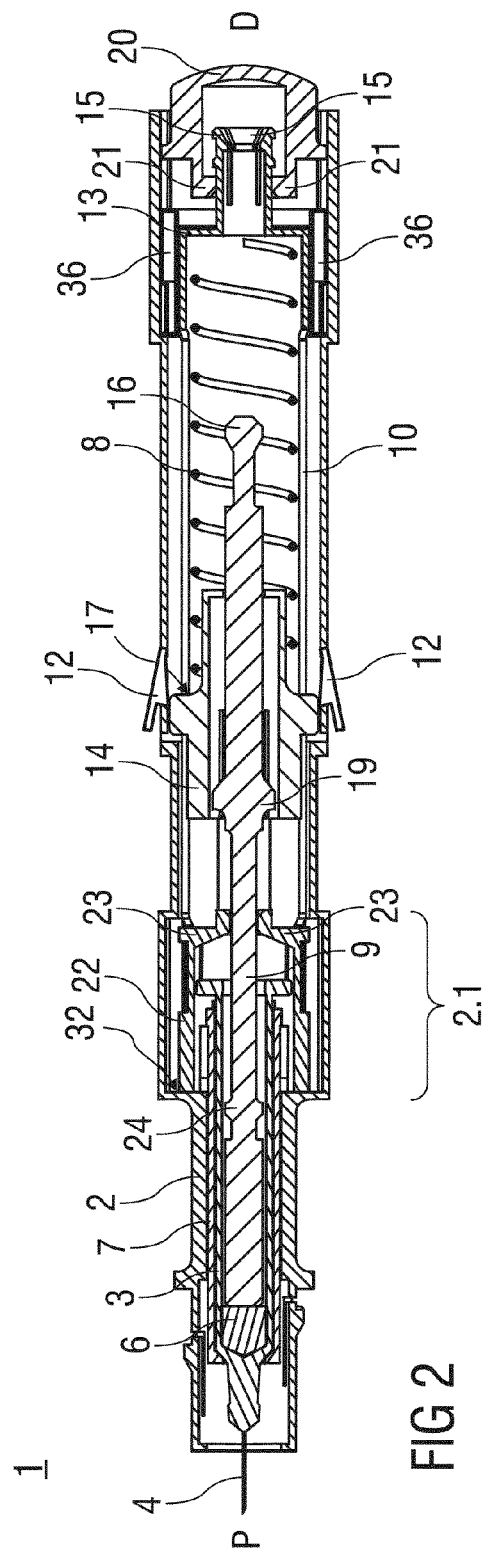
FIG 2

US 9,463,282 B2

ARRANGEMENT FOR COUPLING A PLUNGER TO EITHER A SYRINGE OR A STOPPER

CROSS REFERENCE TO RELATED APPLICATIONS

The present application is a U.S. National Phase Application pursuant to 35 U.S.C. §371 of International Application No. PCT/EP2011/067488 filed Oct. 6, 2011, which claims priority to European Patent Application No. 10186978.2 filed Oct. 8, 2010 and U.S. Provisional Patent Application No. 61/432,261 filed Jan. 13, 2011. The entire disclosure contents of these applications are herewith incorporated by reference into the present application.

FIELD OF INVENTION

The invention relates to an arrangement for coupling a plunger to either a syringe or a stopper in order to avoid a so called wet injection.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

In some conventional art auto-injectors the syringe and needle are forwarded for needle insertion by exerting load onto the stopper of the syringe. Resistance to needle penetration into the skin and inertia of the syringe and needle may result in a resisting force which is close to or greater than the friction force of the stopper in the syringe. As the syringe is urged forwards for needle insertion by applying force to the stopper, the stopper may then also move in the syringe. This can cause a so called wet injection, i.e. liquid medicament leaking out of the needle during needle insertion.

SUMMARY

It is an object of the present invention to provide a means for avoiding a liquid medicament leaking out of a needle before the needle is inserted into an injection site.

The object is achieved by an arrangement for coupling a plunger to either a syringe or a stopper according to claim 1.

Preferred embodiments of the invention are given in the dependent claims.

In the context of this specification the term proximal refers to the direction pointing towards the patient during an injection while the term distal refers to the opposite direction pointing away from the patient.

According to the invention, an arrangement for coupling a plunger to either a syringe or a stopper arranged in the syringe comprises a syringe holder which is slidably arranged in a housing and coupled for joint axial movement with the syringe. The syringe holder is provided with at least one (preferably at least two) resilient syringe holder arm arranged distally. The syringe holder arm has an inclined surface for bearing against a shoulder, which is arranged at the plunger. The syringe holder arm is supportable by an inner surface of the housing in order to prevent it from being flexed outward in a first position. A widened portion is provided in the housing for allowing the syringe holder arm to flex outwards and disconnect from the plunger when in a more proximal position so as to switch load of the plunger from the syringe to the stopper. As long as the syringe holder arm is supported by the inner surface the shoulder pushes the syringe holder, syringe carrier and syringe forward while no load is exerted onto the stopper. A hollow needle arranged at the syringe is inserted into an injection site, e.g. a patient's skin without a wet injection, i.e. liquid medicament leaking out of the needle. When the syringe holder arm reaches the widened portion during the forward movement in proximal direction the syringe holder arm may flex out and allows the second shoulder of the plunger to slip through. Now the plunger no longer pushes against the syringe holder but against the stopper for expelling the medicament from the syringe and injecting it into or through the patient's skin. This allows for defining the moment to start injecting the medicament.

The arrangement for coupling the plunger to either the syringe or the stopper may be applied in any auto-injector having a plunger for forwarding a force of a drive means to a syringe with a stopper. The primary advantage of this arrangement ensures the load from the drive means is not transferred directly to the stopper until the needle is inserted in the patient, thus avoiding a wet injection.

In one embodiment, the arrangement for coupling the plunger to either the syringe or the stopper is applied in an auto-injector for administering a dose of a liquid medicament, comprising:
an elongate housing arranged to contain a syringe with a hollow needle and a stopper for sealing the syringe and displacing the medicament, the housing having a distal end and a proximal end with an orifice intended to be applied against an injection site, wherein the syringe is slidably arranged with respect to the housing,
drive means, capable of, upon activation:
pushing the needle from a covered position inside the housing into an advanced position through the orifice and past the proximal end via a plunger,
operating the syringe to supply the dose of medicament via the plunger, and
activating means arranged to block the drive means prior to manual operation and capable of, upon manual operation, activating the drive means for injection, Preferably, the drive means is a spring means, wherein the activating means is arranged to lock the spring means in a pressurized state prior to manual operation and capable of, upon manual operation, releasing the spring means for injection.

The drive means may be capable of retracting the syringe with the needle into the covered position after delivering the medicament.

The spring means may be a single compression spring arranged to be grounded at a distal end in the housing for advancing the needle and for injecting the dose of medicament. The force of the compression spring is forwarded to the needle and/or the syringe via the plunger. The compression spring is arranged to have its ground in the housing switched to its proximal end for retracting the syringe when the injection of the medicament is at least nearly finished.

The single compression spring is used for inserting the needle, fully emptying the syringe and retracting the syringe and needle to a safe position after injection. Thus a second spring for withdrawing the syringe and needle, which is a motion with an opposite sense compared to advancing the syringe and injecting the dose, is not required. While the distal end of the compression spring is grounded the proximal end moves the syringe forward for inserting the needle and carries on to the injection by pushing on the stopper. When the injection is at least nearly finished the compression spring bottoms out at its proximal end, resulting in the proximal end being grounded in the housing. At the same time the distal end of the compression spring is released from its ground in the housing. The compression spring is now pulling the syringe in the opposite direction.

The auto-injector has a particularly low part count compared to most conventional auto-injectors. The use of just one compression spring reduces the amount of metal needed and thus consequently reduces weight and manufacturing costs.

In one embodiment of the invention a retraction sleeve is axially movable arranged in the housing. At least one latch is provided for axially fixing the retraction sleeve in a maximum proximal position. The compression spring is arranged inside the retraction sleeve with its distal end bearing against a distal end face of the retraction sleeve and with its proximal end bearing against a thrust face of a decoupling member. The decoupling member is arranged to decouple the latch when being moved in proximal direction nearly into a maximum proximal position. When decoupled the refraction sleeve is allowed to move in distal direction and retract the needle by means of the spring force which is no longer grounded at its distal end.

At least two resilient decoupling arms are arranged at the decoupling member. The decoupling arms exhibit inner ramped surfaces bearing against a first shoulder of the plunger in proximal direction P. The resilient decoupling arms are supportable by an inner wall of the retraction sleeve in order to prevent the decoupling arms from being flexed outward and slip past the first shoulder. In this state the plunger may be pushed in proximal direction by the decoupling member pushing against the first shoulder in order to insert the needle and inject the dose. At least one aperture is arranged in the refraction sleeve allowing the decoupling arms to be flexed outward by the first shoulder thus allowing the first shoulder to slip through the decoupling arms in proximal direction. This may happen when the injection is at least nearly finished. The decoupled plunger allows the syringe and needle to be refracted since it is no longer bearing against the decoupling member.

In one embodiment a stud may be arranged at the distal end of the plunger. The retraction sleeve may have two or more resilient arms distally from the end face for holding the stud. The stud and/or the resilient arms have ramp features. Thus the resilient arms may be pushed apart by the stud when the plunger is moved in proximal direction. The activating means comprise a trigger button arranged at the distal end of the auto-injector. The trigger button is axially moveable and has at least two rigid retainers for preventing the resilient arms from being flexed outward when the trigger button is in a maximum distal position. Upon pushing the trigger button in proximal direction the retainers are moved in proximal direction in a manner to allow the resilient arms to be flexed out by the stud biased by the compression spring in proximal direction. Thus the stud is allowed to slip past the resilient arms in proximal direction under load of the compression spring in order to start a needle insertion/injection/retraction cycle. The main advantages of this trigger mechanism are its simplicity, the low part count and a high reliability.

In order to reduce the risk of unintentionally triggering the auto-injector a safety button may be arranged laterally at the housing. The safety button has an interlock for preventing the trigger button from being pushed. The safety button is arranged to pull the interlock outward when operated thus allowing the trigger button to be pushed. For this purpose the safety button may be pivoted in the housing or it may be cast in one piece with the housing in a manner to be pivoted somewhere in the middle so pushing one end inwards causes the other end to be pulled outwards.

Consequently, in order to operate the trigger button the safety button has to be pushed first so the auto-injector cannot be operated unintentionally. Another advantage of the lateral safety button is that the risk of operating the auto-injector in the wrong orientation and injecting into the thumb is reduced.

In a preferred embodiment of the invention a delay box is arranged for slowing down the motion of the retraction sleeve. The latches are arranged to be disengaged by the decoupling member before the stopper has reached a maximum proximal position in the syringe. The apertures are arranged to meet the decoupling arms after the stopper has reached its maximum proximal position by means of the motion of the retraction sleeve. A gap is provided between a front face of the retraction sleeve and the syringe holder in their respective maximum proximal positions. The gap allows the retraction sleeve to travel a distance before retracting the syringe holder so the syringe holder is retracted after the decoupling arms met the apertures.

Triggering the retraction when the stopper exactly reaches the end of its travel is a problem due to tolerances when manufacturing the syringe and stopper. Due to these tolerances the position of the stopper at the end of its travel is not repeatable. Consequently, in some cases the stopper would prematurely bottom out so the retraction would not be triggered at all. In other cases the retraction would be triggered before the stopper bottomed so residual medicament would remain in the syringe.

Releasing the retraction sleeve from the housing a certain amount of time or travel before the stopper bottoms out in the syringe avoids the risk of stalling the retraction by the stopper hitting the end of the syringe prematurely. The damped backward motion of the retraction sleeve due to the delay box allows the plunger and stopper to finish their forward travel so the syringe is entirely emptied. The apertures of the retraction sleeve and the decoupling arms, which are now moving in opposite directions, meet after the stopper and plunger have stopped in order to decouple the decoupling member from the plunger. Due to the gap between the front face and the syringe holder the retraction sleeve is not immediately dragging the syringe back in distal direction when starting to move back. When the retraction sleeve has travelled back far enough to close the gap the stopper has already bottomed out and the plunger has been decoupled from the decoupling member. As soon as the gap is closed the syringe holder, the syringe, the hollow needle and the plunger are dragged back in the distal direction.

Thus both problems are solved, reliably retracting the hollow needle to a safe position and fully emptying the syringe which is particularly desirable with expensive drugs. Emptying the syringe is also important for dosage accuracy.

The delay box may comprise a circumferential outer wall with a back collar attached to the housing and a circumferential inner wall with a front collar attached to the retraction sleeve. A volume is defined between the outer wall and inner wall, the volume sealed by the back collar and front collar and filled with a viscous fluid. At least one hole is arranged in the delay box for allowing the viscous fluid to be pushed out as the volume decreases due to motion of the retraction sleeve. This is a particularly simple and cost-efficient way to damp the backward motion of the retraction sleeve.

Usually the hollow needle is equipped with a protective needle shield for keeping the needle sterile and preventing it from being mechanically damaged. The protective needle shield is attached to the needle when the auto-injector or the syringe is assembled.

Preferably a cap is provided at the proximal end of the housing. A sheet metal clip is attached to the cap for joint axial movement and independent rotation. The sheet metal clip is arranged to extend through an orifice into the housing when the cap is attached to the housing. The sheet metal clip comprises at least two barbs snapped into a circumferential notch or behind a shoulder of the protective needle shield. This allows for automatically engaging the sheet metal clip with the protective needle shield during assembly. When the cap is removed from the housing in preparation of an injection the protective needle shield is reliably removed without exposing the user to too high a risk of injuring themselves.

The cap may be attachable to the housing by a screw connection. This allows for a low force removal of the protective needle shield.

The housing may have at least one viewing window for inspecting the syringe.

In another embodiment an interlock sleeve is telescoped in the proximal end of the housing, the interlock sleeve translatable in longitudinal direction between a proximal position and a distal position and biased in proximal direction in a manner to protrude from the housing in the proximal position, wherein in its proximal position the interlock sleeve is arranged to be coupled to the syringe in the syringe's retracted position for joint axial movement and wherein the interlock sleeve in its distal position is arranged to allow decoupling of the syringe.

In an as delivered state of the auto-injector the interlock sleeve is in its proximal position protruding from the proximal end of the housing. The syringe and needle are in their retracted position. As the interlock sleeve and the syringe are coupled for joint axial movement the syringe and needle cannot advance even if the spring means were inadvertently released by operating the activating means. Thus the needle remains in its covered position. In order to trigger an injection the auto-injector has to be pressed with its proximal end against an injection site, e.g. a patient's skin in a manner to translate the interlock sleeve in distal direction into the housing. Thus the syringe is decoupled or allowed to decouple from the interlock sleeve and may now translate so as to move the needle into its advanced position for piercing the patient's skin. Before the syringe and needle actually translate in proximal direction the activating means has to be operated so as to release the drive spring. The probability for inadvertent operation of the auto-injector thus decreases due to the requirement of two user actions, pressing the auto-injector against the injection site and operating the activating means.

In another embodiment of the invention the activating means may comprise a trigger button in the shape of a wrap-over sleeve button arranged over the distal end of the auto-injector. The trigger button extends at least almost over the whole length of the auto-injector. The trigger button is arranged to release the drive spring upon translation in proximal direction. In order to trigger an injection the auto-injector has to be pressed against an injection site, e.g. a patient's skin. A user, e.g. the patient or a caregiver, grabs the wrap-over sleeve button with their whole hand and pushes against the injection site. Consequently, the trigger button translates in proximal direction and releases the drive spring for starting the injection cycle. This embodiment is particularly well suited for people with dexterity problems since, as opposed to conventional art auto-injectors, triggering does not require operation of small buttons by single fingers. Instead, the whole hand is used.

In an alternative embodiment the activating means is arranged as a trigger button laterally arranged on the housing. A lateral trigger button can be easier to operate for people with dexterity problems.

In yet another embodiment an interlock sleeve is telescoped in the proximal end of the housing, the interlock sleeve translatable in longitudinal direction between a proximal position and a distal position and biased in proximal direction in a manner to protrude from the housing in the proximal position. The activating means comprises a trigger button arranged at the distal end of the auto-injector. The trigger button is locked, thereby preventing actuation when the interlock sleeve is in its proximal position in an as delivered state. Translation of the interlock sleeve unlocks the trigger button so as to allow actuation.

This results in an auto-injector with a sequenced operation. In the as delivered state the interlock sleeve is in its proximal position protruding from the proximal end of the housing. The syringe and needle are in their retracted position. In order to trigger an injection the auto-injector has to be pressed with its proximal end against an injection site, e.g. a patient's skin in a manner to translate the interlock sleeve in distal direction into the housing. This translation allows the trigger button to be actuated for eventually releasing the drive spring and start an injection cycle. The probability for inadvertent operation of the auto-injector decreases due to the requirement of two sequenced user actions, pressing the auto-injector against the injection site and operating the activating means.

In an improved embodiment the aperture in the retraction sleeve extends at least almost to the position of the decoupling arm in the as delivered state up to the decoupling arms position at the end of dose. The aperture is arranged to be angularly misaligned with respect to the decoupling arm when the retraction sleeve is in its proximal position so the plunger does not decouple from the decoupling member. The aperture and the retraction sleeve are also arranged to rotate so as to align the aperture with the decoupling arms upon translation of the retraction sleeve out of the proximal position in distal direction so the plunger and decoupling member decouple from each other thus allowing retraction of the plunger, stopper syringe and needle. Hence, the syringe and the needle may be refracted at any point of the injection cycle.

In yet another embodiment a damper is arranged around the plunger and engaged with the plunger by a spline so as to cause rotation of either the plunger or the damper at least during part of a translation of the plunger in proximal direction. Thus the load of the drive spring is shared between the translation and the rotation in order to adapt insertion and dispense characteristics of the auto-injector. The force of the drive spring is highest when compressed. With increasing expansion of the released drive spring its force decreases. The characteristics of the drive spring have to be chosen so as to ensure that the spring force is sufficient to retract the needle at the end of the injection when the spring is almost entirely expanded and its force is lowest. Thus the spring force may be inconveniently high during needle insertion or injection. The damper splined to the plunger may be used to compensate for this effect.

The damper and plunger may be arranged to cause rotation only during operation of the syringe to supply the dose of medicament, i.e. during injection. During needle insertion the translation is not damped since a rapid needle insertion is thought to be less painful for a patient. Damping the translation during injection serves for decreasing an injection rate which is also considered more convenient for the patient. The spline engagement may be arranged to be disengaged during needle retraction so as to ensure a fast needle retraction.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

The delay box may be employed with other types of auto-injectors.

The cap with the sheet metal spring may also be applied with other auto-injectors and injection devices.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus, are not limiting of the present invention, and wherein.

Corresponding parts are marked with the same reference symbols in all figures.

DETAILED DESCRIPTION

Figure 1:
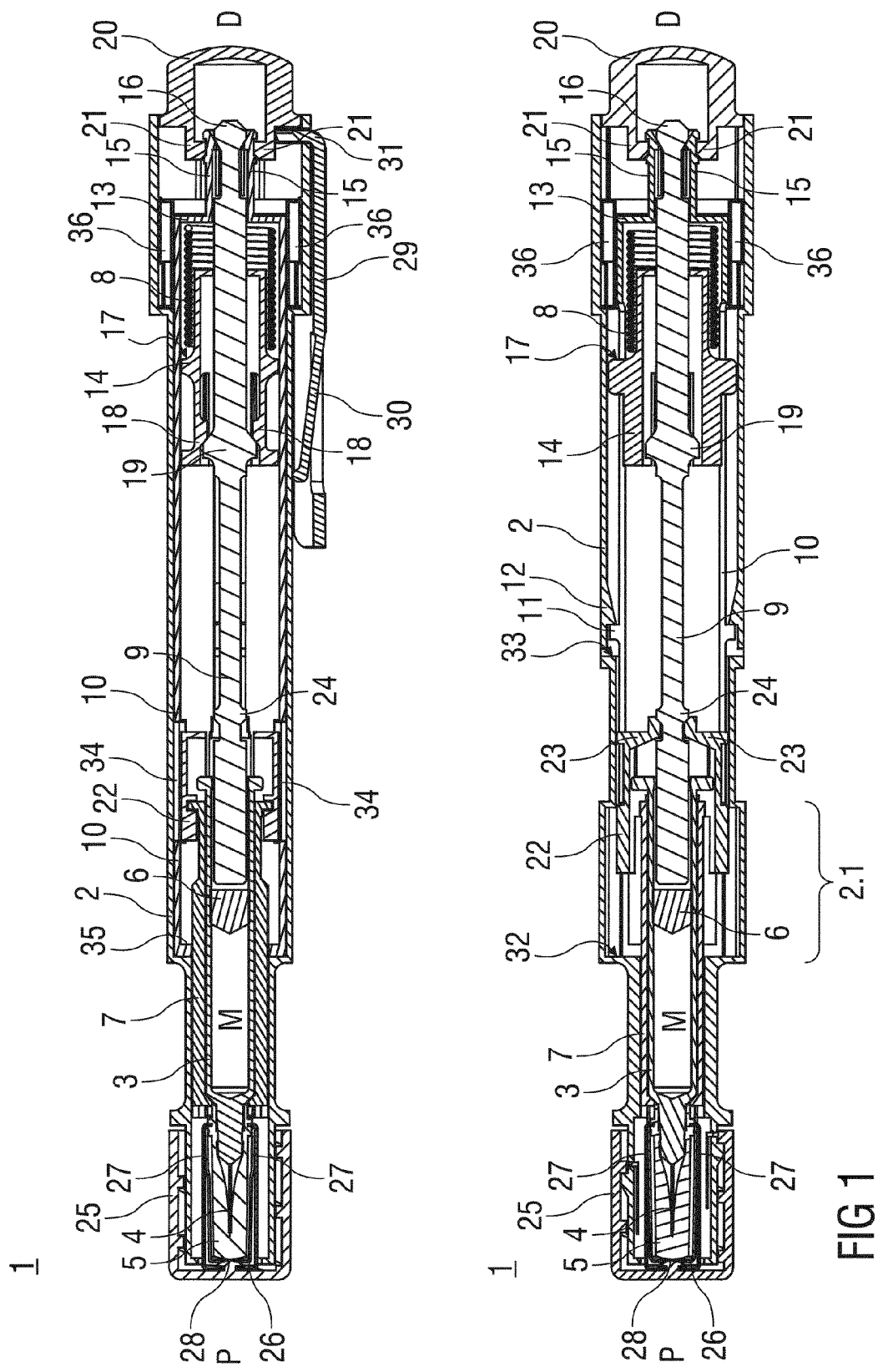
FIG. 1 are two longitudinal sections of an auto-injector with a single compression spring for advancing a syringe with a needle, injecting a dose of medicament and retracting the syringe and needle, the auto-injector as-delivered, FIG. 2 are two longitudinal sections of the auto-injector with the syringe and needle advanced and the dose expelled from the syringe.
Figure 3:
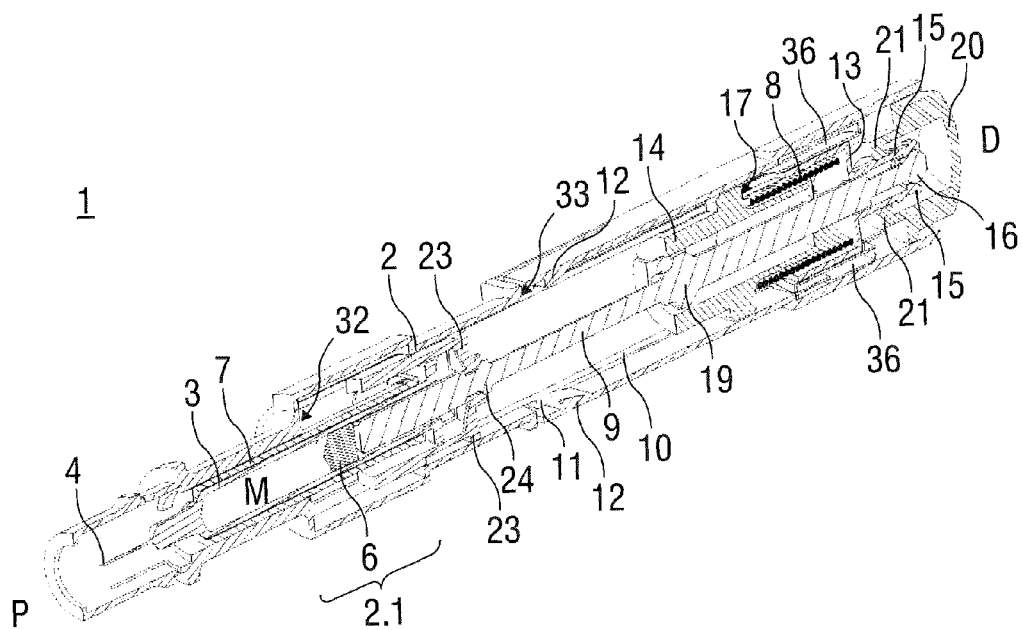
FIG. 3 is a perspective sectional view of the auto-injector in the initial state of FIG. 1.

FIG. 1 shows two longitudinal sections in different section planes of an auto-injector 1, the different section planes approximately 90° rotated to each other. The auto-injector 1 comprises an elongate housing 2. A syringe 3, e.g. a Hypak syringe, with a hollow needle 4 is arranged in a proximal part of the auto-injector 1. When the auto-injector 1 or the syringe 3 is assembled a protective needle shield 5 is attached to the needle 4. A stopper 6 is arranged for sealing the syringe 3 distally and for displacing a liquid medicament M through the hollow needle 4. The syringe 3 is held in a tubular syringe carrier 7 and supported at its proximal end therein. A single compression spring 8 is arranged in a distal part of the auto-injector 1. A plunger 9 is arranged for forwarding the spring force of the compression spring 8.

Inside the housing 2 a retraction sleeve 10 is slidably arranged. Before the injection is triggered as shown in FIG. 1 the retraction sleeve 10 is in a maximum proximal position and prevented from moving in distal direction D by means of stops 11 caught behind latches 12 in the housing 2. A distal end of the compression spring 8 bears against an end face 13 of the retraction sleeve 10. Due to the stops 11 and latches 12 the force of the compression spring 8 is thus reacted into the housing 2. The proximal end of the compression spring 8 bears against a decoupling member 14 arranged around the plunger 9. Distally from the end face 13 the retraction sleeve has two or more resilient arms 15 for holding a stud 16 and keeping it from being moved in proximal direction P. The stud 16 is arranged at the distal end of the plunger 9. The stud 16 and the resilient arms 15 have corresponding ramp features for pushing the resilient arms 15 apart in order to allow the stud 16 and the plunger 9 to move in proximal direction P.

The decoupling member 14 comprises a thrust face 17 for bearing against a proximal end of the compression spring 8.

Proximally from the thrust face 17 two or more resilient decoupling arms 18 are provided at the decoupling member 14, the decoupling arms 18 having inner ramped surfaces bearing against a first shoulder 19 in the plunger 9 in proximal direction P. The resilient decoupling arms 18 are supported by an inner wall of the retraction sleeve 10 in this situation so they cannot flex outward and slip past the first shoulder 19.

A trigger button 20 is arranged at the distal end D of the auto-injector 1. The trigger button 20 may be pushed in proximal direction P in order to start an injection. As long as the trigger button 20 is not pushed the resilient arms 15 are caught between two or more retainers 21 arranged at the trigger button 20 so the resilient arms 15 cannot flex outward and the stud 16 although proximally biased by the compression spring 8 cannot slip through.

The syringe carrier 7 is engaged for joint axial movement with a syringe holder 22 which is slidably arranged in the retraction sleeve 10. The syringe holder 22 is provided with two or more resilient syringe holder arms 23 arranged distally. The syringe holder arms 23 have a respective inclined surface for bearing against a second shoulder 24 in the plunger 9 arranged proximally from the first shoulder 19. In the initial position shown in FIG. 1 the syringe holder arms 23 are supported by an inner surface of the housing 2 so they cannot flex outward and the second shoulder 24 cannot slip through. In order to support the syringe holder arms 23 at the housing 2 a respective number of apertures are provided in the retraction sleeve 10.

Figure 6:
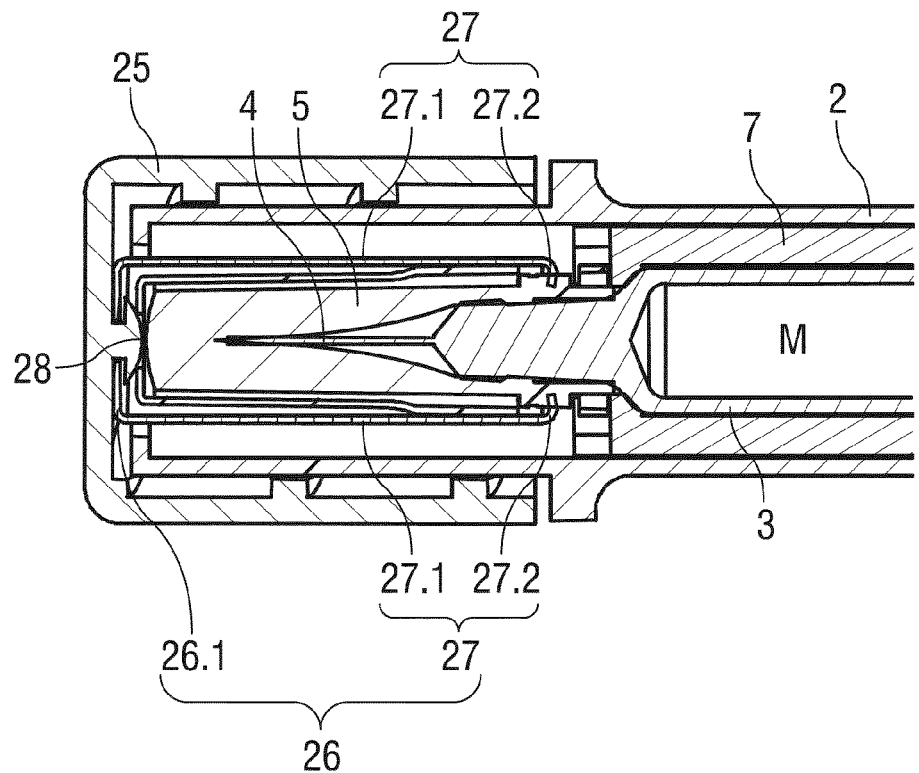
FIG. 6 is a detailed view of the proximal end of the autoinjector showing the cap and needle shield remover.

FIG. 1 shows the auto-injector 1 as-delivered with a cap 25 screwed onto to the proximal end P of the auto-injector 1. FIG. 6 shows details of the proximal end P with the cap 25. The cap 25 comprises a sheet metal clip 26 with two or more barbs 27 extending through an orifice into the proximal end P of the auto-injector 1. The sheet metal clip 26 is mounted to the cap 25 for joint axial movement with respect to a longitudinal axis of the auto-injector 1. However, the sheet metal clip 26 may rotate independently from the cap 25. This may be achieved by attaching the sheet metal clip 26 with a hole in its base onto a pin protruding inwardly from the cap 25 and deforming the pin to form a mushroom-shaped closing head 28 so as to prevent the sheet metal clip 26 from being removed while allowing some clearance for the sheet metal clip 26 to rotate. When the cap 25 is screwed onto the proximal P end of the auto-injector 1 the barbs 27 are pushed down the protective needle shield 5 and snap into a circumferential notch arranged in the protective needle shield 5 or behind a shoulder thereof.

When a user wants to operate the auto-injector 1 the first step is to unscrew the cap 25. Thus the barbs 27 pull the protective needle shield 5 off the syringe 3 in proximal direction P and through the orifice making the syringe 3 ready to be used.

A safety button 29 is arranged laterally at the distal part of the housing 2. The safety button 29 serves for interlocking with the trigger button 20 in a manner to prevent the trigger button 20 from being inadvertently operated without the safety button 29 being released from a first blocking position.

Consequently, in order to operate the trigger button 20 the safety button 29 has to be pushed transversally with respect to the longitudinal axis against the force of a spring element 30 which is formed in the safety button 29. The safety button 29 is pivoted in the middle so pushing the proximal end of the safety button 29 inward pulls an interlock 31 at its proximal end obstructing the trigger button 20 outward so the trigger button 20 can be pushed.

When the trigger button 20 is pushed the retainers 21 are pushed in proximal direction P so the resilient arms 15 are allowed to flex outward. Under load of the compression spring 8 the inclined surfaces of the stud 16 force the resilient arms 15 apart until the stud 16 can slip through.

The second shoulder 24 pushes the syringe holder 22, syringe carrier 7 and syringe 3 forward while no load is exerted onto the stopper 6. The hollow needle 4 appears from the proximal end P and is inserted into an injection site, e.g. a patient's skin.

The forward movement continues until the syringe holder 22 bottoms out at a first abutment 32 in the housing 2 (see FIG. 2). The travel from the initial position (cf. FIG. 1) up to this point defines an injection depth, i.e. needle insertion depth.

When the syringe holder 22 has nearly bottomed out the resilient syringe holder arms 23 have reached a widened portion 2.1 of the housing 2 where they are no longer supported by the inner wall of the housing 2. However, since the force required to insert the needle 4 is relatively low the second shoulder 24 will continue to drive forward the syringe holder 22 until proximal travel is halted at the first abutment 32. At this point the syringe holder arms 23 are flexed out by the continued force of the second shoulder 24 and allow it to slip through. Now the plunger 9 no longer pushes against the syringe holder 22 but against the stopper 6 for expelling the medicament M from the syringe 3 and injecting it into or through the patient's skin.

When the stopper 6 has nearly bottomed out in the syringe 3 (cf. FIG. 2) the decoupling member 14 has reached a position where it pushes against the latches 12 in a manner to decouple the retraction sleeve 10 from the housing 2, so the retraction sleeve 10 may slide in distal direction D. Thus the compression spring 8 is no longer grounded with its distal end in the housing 2. Instead, as soon as the decoupling member 14 has bottomed out at a second abutment 33 the proximal end of the compression spring 8 gets grounded in the housing while the distal end is pulling the retraction sleeve 10 in distal direction D.

Figure 4:
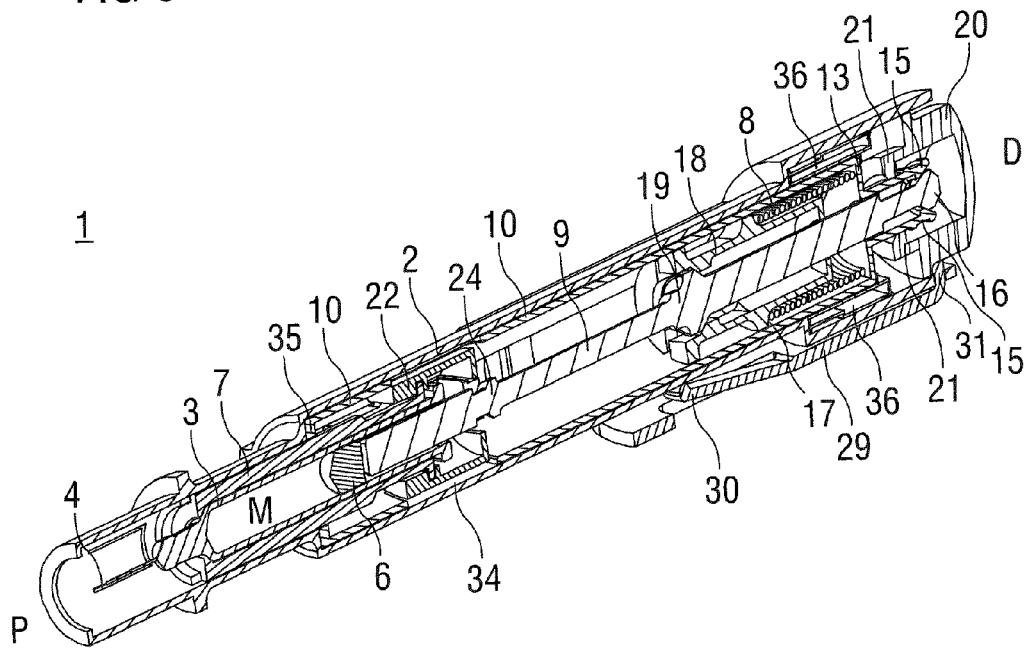
FIG. 4 is another perspective sectional view of the auto-injector of FIG. 3.

Just before the decoupling member 14 decouples the retraction sleeve 10 from the housing 2 the decoupling arms 18 reach an aperture 34 in the retraction sleeve 10 (see FIG. 4) so they are no longer kept from being flexed outward. The decoupling arms 18 are thus pushed outward by the first shoulder 19 pushing against its ramped surfaces so the first shoulder 19 slips through in distal direction as soon as the decoupling member 14 has hit the second abutment 33.

The syringe holder 22 is taken along in distal direction D by the retraction sleeve 10, e.g. by a front face 35. Thus the syringe 3 and needle 4 are retracted into a safe position inside the housing 2, e.g. into the initial position. The plunger 9, no longer bearing against the decoupling arms 18 is pulled back too.

Figure 5:
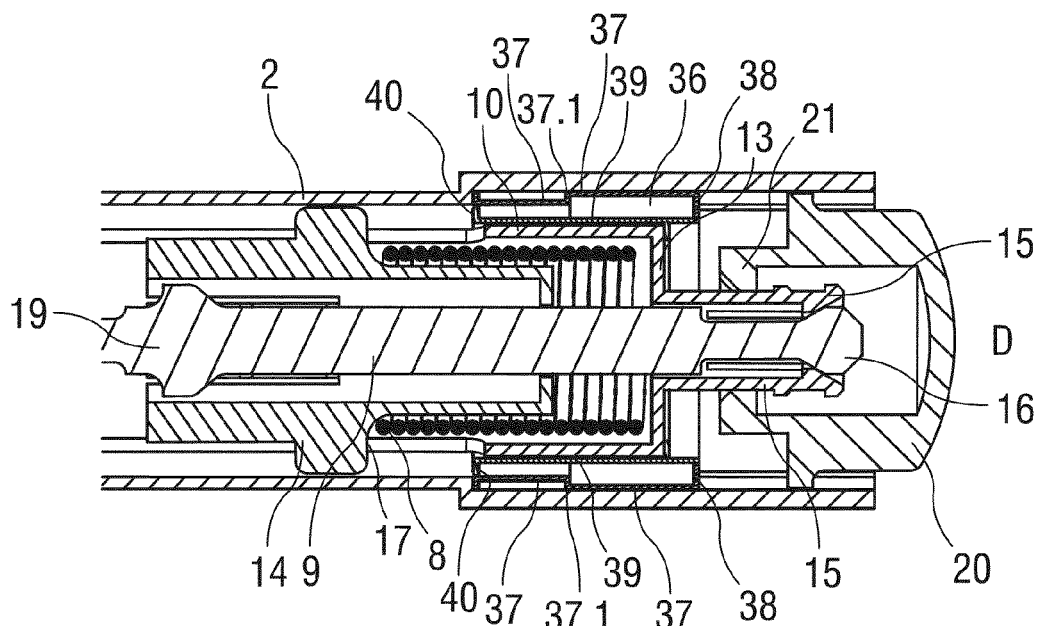
FIG. 5 is a detail view of the distal end of the auto-injector with a delay box.

In the distal part of the auto-injector 1 a delay box 36 is arranged (see FIG. 5 for details). The delay box 36 comprises a circumferential outer wall 37 with a back collar 38 attached to the housing 2 and a circumferential inner wall 39 with a front collar 40 attached to the refraction sleeve 10. A volume between the outer wall 37 and inner wall 39 is filled with a viscous fluid, such as silicon grease. As the refraction sleeve 10 is moved in distal direction D the inner wall 39 glides along the outer wall 37 wherein the back collar 38 and front collar 40 increasingly reduce the volume. One or more holes (not shown) provided in a part of the delay box 36 allow the viscous fluid to be pushed out as the volume decreases. The force required to do this slows down the motion of the retraction sleeve 10.

The retraction sleeve 10 is released by the decoupling member 14 from the housing 2 a certain amount of time or travel before the stopper 6 bottoms out in the syringe 3 and the distal motion of the retraction sleeve 10 begins. The motion of the retraction sleeve 10 is slowed down by the delay box 36. Due to a gap 41 between the front face 35 and the syringe holder 22 the retraction sleeve 10 is not yet dragging the syringe back in distal direction D. The plunger 9 is still pushing against the stopper 6 and expelling residual medicament M. As the stopper 6 hits the proximal end of the syringe 3 the stopper 6 and plunger 9 stop while the retraction sleeve 10 is still slowly moving back in distal direction D. The apertures 34 now meet the decoupling arms 18 allowing them to flex out and the plunger 9 to come clear. The retraction sleeve 10 has now traveled back far enough to close the gap 41 so the syringe holder 22, syringe carrier 7, syringe 3, needle 4 and plunger 9 are dragged back in distal direction D.

The cap 25 and the delay box 36 are not restricted to be used with the auto-injector 1 shown in the embodiments. Instead the cap 25 may be combined with any kind of auto-injector with the needle hidden in the housing prior to an injection. The delay box may be combined with any kind of auto-injector for ensuring full delivery of the syringe's contents and reliable triggering of the refraction, irrespective of the spring means or driving means used in the respective auto-injector.

The housing 2 may have at least one viewing window for inspecting the syringe 3.

The auto-injector 1 may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

The aforementioned arrangement for coupling the plunger 9 to either, the syringe 3 or the stopper 6, may be applied in any auto-injector having a plunger for forwarding a force of a drive means to a syringe with a stopper. The primary advantage of this arrangement ensures the load from the drive means is not transferred directly to the stopper until the needle is inserted in the patient, thus avoiding a wet injection. The arrangement comprises the syringe holder 22 and associated syringe holder arms 23, a shoulder (e.g. the second shoulder 24) on the plunger 9, the support of the holder arms 23 by an inner surface in order to prevent them from flexing out in a first position and, a widened portion 2.1 for allowing them to flex radially and to disconnect from the plunger when in a more proximal position. The syringe carrier 7 is also a key part of this arrangement. The syringe holder 22 is locked on to the syringe carrier 7, not on to the syringe directly. Therefore, friction between the syringe 3 and the carrier 7 is critical for avoidance of a wet injection. When the syringe holder 22 and syringe carrier 7 are pushed forwards, the resistance of the needle 5 penetrating the skin, and the inertia of the filled syringe 3 will act directly on the syringe 3 tending to force it backwards in the syringe carrier 7. If friction is inadequate between syringe carrier 7 and syringe 3, the syringe 3 will slide backwards, the stopper 6 will come into contact with the end of the plunger 9, and a wet injection may result. Friction between the syringe 3 and the syringe carrier 7 has therefore to be sufficiently high, e. g. by respectively specifying an inner diameter of the syringe carrier 7 relative to an external diameter of the syringe 3 and/or by choosing a high friction material for the syringe carrier 7 or applying a high friction coating to the syringe 3 and/or syringe carrier 7.

The spring means or other drive means, the ability to retract the syringe or to forward a needle shroud after injection and other features described herein are not required for the prevention of a wet injection.

The invention claimed is:

1. An arrangement for coupling a plunger to either a syringe or a stopper arranged in the syringe, the arrangement comprising:

a syringe holder configured to be slidably arranged in a housing and configured to be coupled to the syringe, the syringe holder comprising a resilient syringe holder arm having a first end and a second end, the first end of the syringe holder arm being attached to a distal end of the syringe holder, and the second end of the syringe holder arm having an inclined surface for bearing against a shoulder of the plunger, wherein the syringe holder arm is configured to be supported by a first portion of an inner surface of the housing to inhibit the syringe holder arm from being flexed outward when the syringe holder arm is in a first position, wherein the syringe holder arm is configured such that the inclined surface of the second end of the syringe holder arm engages the shoulder of the plunger to connect the syringe holder arm to the plunger when the syringe holder arm is in the first position, and wherein the syringe holder arm is configured to flex outwards into a second portion of the inner surface of the housing and to disengage the inclined surface of the second end from the shoulder of the plunger such that the syringe holder arm is disconnected from the plunger and engages with the stopper when the syringe holder arm is in a second position proximal to the first position.

2. The arrangement according to claim 1, wherein the syringe holder arm is one of at least two syringe holder arms attached to the syringe holder.

3. The arrangement according to claim 1, further comprising a syringe carrier arranged for holding the syringe and supporting the syringe at a proximal end of the syringe, the syringe carrier and the syringe holder being coupled for joint axial motion through the housing.

4. An auto-injector for administering a dose of medicament, comprising:

an elongate housing comprising an inner surface having a first portion and a second portion, the second portion being wider than the first portion, the housing being arranged to contain a syringe in a slidable manner within the housing, and the syringe comprising a hollow needle and a stopper for sealing the syringe and displacing the medicament, and the housing having a distal end and a proximal end with an orifice intended to be applied against an injection site;

a drive mechanism arranged in the housing, the drive mechanism being configured to, upon activation, push the needle from a covered position inside the housing into an advanced position through the orifice and past the proximal end of the housing via a plunger, and operate the syringe to supply the dose of medicament via the plunger;

an activating mechanism arranged in the housing to block the drive mechanism prior to manual operation of the activating mechanism, the activating mechanism being configured to, upon manual operation, activate the drive mechanism for injection; and a syringe holder slidably arranged in a housing and configured to be coupled to the syringe, the syringe holder comprising a resilient syringe holder arm having a first end and a second end, the first end of the syringe holder arm being attached to a distal end of the syringe holder, and the second end of the syringe holder arm having an inclined surface for bearing against a shoulder of the plunger, wherein the syringe holder arm is configured to be supported by a first portion of an inner surface of the housing to inhibit the syringe holder arm from being flexed outward when the syringe holder arm is in a first position, wherein the syringe holder arm is configured such that the inclined surface of the second end of the syringe holder arm engages the shoulder of the plunger to connect the syringe holder arm to the plunger when the syringe holder arm is in the first position, and wherein the syringe holder arm is configured to flex outwards into a second portion of the inner surface of the housing and to disengage the inclined surface of the second end from the shoulder of the plunger such that the syringe holder arm is disconnected from the plunger and engages with the stopper when the syringe holder arm is in a second position proximal to the first position.

5. The auto-injector according to claim 4, wherein:
the drive mechanism comprises a spring, and
the activating mechanism is arranged to lock the spring in a pressurized state prior to manual operation and is configured to, upon manual operation, release the spring for injection.

6. The auto-injector according to claim 5, wherein the spring is a single compression spring having a distal end grounded in the housing and a proximal end configured to couple to the plunger for advancing the needle and for injecting the dose of medicament, the compression spring being arranged to have its ground in the housing switched to its proximal end for retracting the syringe.

7. The auto-injector according to claim 6, further comprising:
a retraction sleeve axially movably arranged in the housing,
a latch arranged in the housing for axially fixing the retraction sleeve in a maximum proximal position, and
a decoupling member arranged in the housing to decouple the latch to enable the retraction sleeve to move in a distal direction to retract the needle when the decoupling member is moved in a proximal direction nearly into a maximum proximal position,
wherein the compression spring is arranged inside the retraction sleeve with a distal end of the compression spring bearing against a distal end face of the retraction sleeve and with the proximal end of the compression spring bearing against a thrust face of the decoupling member.

8. The auto-injector according to claim 7, wherein the shoulder of the plunger is a second shoulder, and the auto-injector further comprises:
at least two resilient decoupling arms arranged at the decoupling member, the resilient decoupling arms having inner ramped surfaces bearing against a first shoulder of the plunger in the proximal direction, wherein the resilient decoupling arms are supportable by an inner wall of the retraction sleeve to inhibit the resilient decoupling arms from being flexed outward and slip slipping past the first shoulder, and
at least one aperture arranged in the retraction sleeve and configured to enable the resilient decoupling arms to be flexed outward by the first shoulder such that the first shoulder is movable through the resilient decoupling arms in the proximal direction.

9. The auto-injector according to claim 7, further comprising a stud arranged at a distal end of the plunger,
wherein the retraction sleeve has two or more resilient arms extending distally from the distal end face for holding the stud, the stud and/or the resilient arms having ramp features configured to enable the resilient arms to be pushed apart by the stud when the plunger is moved in the proximal direction,
wherein the activating mechanism comprises a trigger button arranged at the distal end of the housing, the trigger button being axially movable relative to the housing and having at least two rigid retainers for inhibiting the resilient arms from being flexed outward when the trigger button is in a maximum distal position, and
wherein, when the trigger button is pushed in the proximal direction, the retainers are configured to move in the proximal direction to allow the resilient arms to be pushed apart by the stud biased by the compression spring in the proximal direction such that the stud is movable past the resilient arms in the proximal direction.

10. The auto-injector according to claim 8, wherein:
the aperture extends at least almost to a position of the decoupling arms in an as delivered state of the auto-injector,
the aperture is arranged to be angularly misaligned with respect to the decoupling arm when the retraction sleeve is in the maximum proximal position, and
the aperture is arranged to rotate to align with the decoupling when the retraction sleeve is translated out of the maximum proximal position in the distal direction.

11. The arrangement according to claim 1, wherein the first end of the syringe holder arm is rotationally and translationally fixed to the syringe holder.

12. The arrangement according to claim 11, wherein the second end of the syringe holder arm is a free end, and the syringe holder arm is configured to flex such that the first end remains fixed to the syringe holder and the second end moves relative to the first end.

13. The arrangement according to claim 11, wherein the second end of the syringe holder arm comprises an abutment surface that is positioned opposite to the inclined surface, the abutment surface being configured to contact the first portion of the inner surface of the housing to inhibit the syringe holder arm from being flexed outward when the syringe holder arm is in the first position.

14. The arrangement according to claim 13, wherein the abutment surface is configured to deflect into the second portion of the inner surface of the housing and disengage from the housing when the syringe holder arm is moved from the first position to the second position.

15. The arrangement according to claim 1, wherein the plunger is configured such that a load initially exerted by the plunger on the syringe is applied to the stopper when the syringe holder arm is moved to the second position.

16. The auto-injector according to claim 4, wherein the first end of the syringe holder arm is rotationally and translationally fixed to the syringe holder.

17. The auto-injector according to claim 16, wherein the second end of the syringe holder arm is a free end, and the syringe holder arm is configured to flex such that the first end remains fixed to the syringe holder and the second end moves relative to the first end.

18. The auto-injector according to claim 16, wherein the second end of the syringe holder arm comprises an abutment surface that is positioned opposite to the inclined surface, the abutment surface being configured to contact the first portion of the inner surface of the housing to inhibit the syringe holder arm from being flexed outward when the syringe holder arm is in the first position.

19. The auto-injector according to claim 18, wherein the abutment surface is configured to deflect into the second portion of the inner surface of the housing and disengage from the housing when the syringe holder arm is moved from the first position to the second position.

20. The auto-injector according to claim 4, wherein the plunger is configured such that a load initially exerted by the plunger on the syringe is applied to the stopper when the syringe holder arm is moved to the second position.

* * * * *